US00PP30096P3

(12) United States Plant Patent
Danfeng et al.

(10) Patent No.: US PP30,096 P3
(45) Date of Patent: Jan. 15, 2019

(54) ***CAMELLIA* PLANT NAMED 'HA5110'**

(50) Latin Name: *Camellia changii*
Varietal Denomination: HA5110

(71) Applicants: Yan Danfeng, Guangzhou (CN); Liu Xinkai, Guangzhou (CN); Zhao Qiangmin, Guangzhou (CN)

(72) Inventors: Yan Danfeng, Guangzhou (CN); Liu Xinkai, Guangzhou (CN); Zhao Qiangmin, Guangzhou (CN)

(73) Assignee: Palm Eco-Town Development Co., Ltd., Guangzhou (CN)

( * ) Notice: Subject to any disclaimer, the term of this patent is extended or adjusted under 35 U.S.C. 154(b) by 0 days.

(21) Appl. No.: 15/732,757

(22) Filed: Dec. 23, 2017

(65) Prior Publication Data

US 2018/0192563 P1 Jul. 5, 2018

Related U.S. Application Data

(60) Provisional application No. 62/498,661, filed on Dec. 31, 2016.

(51) Int. Cl.
*A01H 5/02* (2018.01)
*A01H 5/12* (2018.01)

(52) U.S. Cl.
USPC ..... Plt./244
CPC ..... *A01H 5/02* (2013.01); *A01H 5/12* (2013.01)

(58) Field of Classification Search
USPC ..... Plt./244, 245
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Camellia* plant named 'HA5110', characterized by its sturdy upright plant habit; moderately vigorous growth habit; freely branching habit, dense and bushy appearance; leathery dark green-colored leaves; long flowering period; light red-colored rose-double to peony-type form flowers; and good garden performance including tolerance to full sunlight conditions.

2 Drawing Sheets

Botanical designation: *Camellia changii.*
Cultivar denomination: 'HA5110'.

BACKGROUND OF THE INVENTION

The present Invention relates to a new and distinct cultivar of *Camellia* plant, botanically known as *Camellia changii*, and hereinafter referred to by the name 'HA5110'.

The new *Camellia* plant is a product of a planned breeding program conducted by the Inventors in Zhaoqing, China. The objective of the breeding program is to create new *Camellia* plants that flower year-round and tolerate full sunlight.

The new *Camellia* plant originated from a cross-pollination conducted by the Inventors in October, 2011 in Zhaoqing, China of an unnamed seedling selection of *Camellia changii*, not patented, as the female, or seed, parent with *Camellia changii* 'Xiari Taige', not patented, as the male, or pollen, parent. The new *Camellia* plant was discovered and selected by the Inventors as a single plant from within the progeny of the stated cross-pollination in a controlled environment in Zhaoqing, China in August, 2013.

Asexual reproduction of the new *Camellia* plant by grafting cuttings onto an unnamed selection of *Camellia gaozhouensis*, not patented, in a controlled greenhouse environment in Zhaoqing, China has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HA5110'. These characteristics in combination distinguish 'HA5110' as a new and distinct cultivar of *Camellia:*

1. Sturdy upright plant habit.
2. Moderately vigorous growth habit.
3. Freely branching habit, dense and bushy appearance.
4. Leathery dark green-colored leaves.
5. Long flowering period.
6. Light red-colored rose-double to peony-type form flowers.
7. Good garden performance, tolerant to full sunlight conditions.

Plants of the new *Camellia* differ from plants of the female parent selection primarily in the following characteristics:

1. Leaves of plants of the new *Camellia* are obovate in shape whereas leaves of plants of the female parent selection are lanceolate in shape.
2. Flowers of plants of the new *Camellia* are rose-double to peony-type in form whereas flowers of the female parent selection are single in form.

Plants of the new *Camellia* differ primarily from plants of the male parent, 'Xiari Taige', in the following characteristics:

1. Leaves of plants of the new *Camellia* are obovate in shape whereas leaves of plants of 'Xiari Taige' are elliptical in shape.

2. Flowers of plants of the new *Camellia* are rose-double to peony-type in form whereas flowers of 'Xiari Taige' are semi-double to peony-type in form.

Plants of the new *Camellia* can be compared to the plants of *Camellia japonica* 'Marie Bracey', not patented. In side-by-side comparisons plants of the new *Camellia* differ from plants of the 'Marie Bracey' in the following characteristics:

1. Leaves of plants of the new *Camellia* are obovate in shape whereas leaves of plants of 'Marie Bracey' are oblong in shape.
2. Flowers of plants of the new *Camellia* are rose-double to peony-type in form whereas flowers of 'Marie Bracey' are semi-double to peony-type in form.
3. Plants of the new *Camellia* flower for a longer period of time than plants of 'Marie Bracey'.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HA5110' grown in an outdoor nursery.

The photograph on the second sheet are close-up views of the lower surface of a typical leaf, typical terminal branches with different stages of developing flower buds, a typical developing flower bud and a typical terminal branch with a fully open flower of 'HA5110'.

DETAILED BOTANICAL DESCRIPTION

The aforementioned photographs and following observations and measurements describe plants grown in Zhaoqing, China in ground beds in an outdoor nursery during the late spring and early summer and under cultural practices typical of commercial *Camellia* production. During the production of the plants, day temperatures ranged from 18° C. to 33° C. and night temperatures ranged from 11° C. to 26° C. Plants were five years old when the photographs and description were taken. In the following description, color references are made to The Royal Horticultural Society Colour Chart, 2007 Edition, except where general terms of ordinary dictionary significance are used.

Botanical classification: *Camellia changii* 'HA5110'.

Parentage:

*Female, or seed, parent.*—Unnamed seedling selection of *Camellia changii*, not patented.

*Male, or pollen, parent.*—*Camellia changii* 'Xiari Taige', not patented.

Propagation:

*Type.*—By grafting cuttings onto a rootstock, an unnamed selection of *Camellia gaozhouensis*, not patented.

*Time to produce a rooted young plant, summer.*—About three months at temperatures about 28° C.

*Time to produce a rooted young plant, winter.*—About four months at temperatures about 8° C.

Plant description:

*Plant form and growth habit.*—Perennial evergreen shrub; sturdy upright plant habit; moderately vigorous growth habit; moderate growth rate.

*Branching habit.*—Freely branching habit; about three primary lateral branches each with about three to four secondary branches; dense and bushy appearance.

*Plant height.*—About 96 cm.

*Plant diameter, area of spread.*—About 58 cm.

*Lateral branch description.*—Length: About 50 cm. Diameter: About 1 cm. Internode length: About 6.3 cm. Strength: Strong. Aspect: Upright to about 10° to 20° from vertical. Texture and luster: Smooth, glabrous; glossy; woody with development. Color, young stems: Close to 165A. Color, older stems: Close to 198A.

*Leaf description.*—Arrangement: Alternate, single. Length: About 9.1 cm. Width: About 4 cm. Shape: Obovate. Apex: Obtuse to acute. Base: Cuneate. Margin: Entire. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper surface: Close to 147A. Developing leaves, lower surface: Close to 137B. Fully expanded leaves, upper surface: Close to 139A; venation, close to 137C; color becoming closer to 137C during the autumn. Fully expanded leaves, lower surface: Close to 137B; venation, close to 146A; color does not change during the autumn.

*Petioles.*—Length: About 1 cm. Diameter: About 3 mm. Texture and luster, upper and lower surfaces: Smooth, glabrous; leathery; matte. Color, upper surface: Close to 143A. Color, lower surface: Close to 143C.

Flower description:

*Flower arrangement and appearance.*—Rose-double to peony-type rotate flowers, flowers terminal and axillary; freely flowering habit with usually about 137 flowers and flower buds developing per plant; flowers face mostly outwardly.

*Natural flowering season.*—Plants of the new *Camellia* flower year-round in Zhaoqing, China.

*Postproduction longevity.*—Plants maintain good flower substance for about three to four days on the plant; flowers persistent.

*Fragrance.*—None detected.

*Flower diameter.*—About 9.1 cm.

*Flower depth.*—About 4.2 cm.

*Flower buds.*—Length: About 2.7 cm. Diameter: About 2.2 cm. Shape: Ovoid. Texture and luster: Smooth, glabrous; leathery; matte. Color: Close to 144A.

*Petals and petaloids.*—Quantity and arrangement: About 43 imbricate petals and petaloids arranged in numerous whorls. Length: About 4.8 cm to 5.1 cm. Width: About 2.6 cm to 2.7 cm. Shape: Obovate. Apex: Obcordate to cordate. Base: Cuneate. Margin: Entire; slightly undulate. Texture and luster, upper and lower surfaces: Smooth, glabrous; silky; matte. Color: When opening and fully opened, upper surface: Close to 51A; venation, close to 51A; color does not change with development. When opening and fully opened, lower surface: Close to 52A; venation, close to 52A; color does not change with development.

*Sepals.*—Quantity and arrangement: About four imbricate sepals arranged in an ovate-shaped calyx. Length: About 1.3 cm. Width: About 9 mm. Shape: Ovate. Apex: Cuspidate. Base: Truncate. Margin: Entire. Texture and luster, upper and lower surfaces: Smooth, glabrous; leathery; matte. Color: When opening, upper surface: Close to N144C. When opening, lower surface: Close to N144D. Fully opened, upper and lower surfaces: Close to N144A.

*Peduncles.*—Length: About 8 mm. Diameter: About 4 mm. Aspect: About 30° to 45° from stem axis. Strength: Strong. Texture and luster: Smooth, glabrous; matte. Color: Close to 146B and 137A.

*Reproductive organs.*—Androecium: Quantity per flower: About 111. Filament length: About 3 cm. Filament color: Close to 38B. Anther shape: Narrowly oblong. Anther size: About 2 mm by 3 mm. Anther color: Close to 14A. Pollen amount: Moderate. Pollen color: Close to 14A. Gynoecium: Quantity of pistils per flower: About five to six. Pistil length: About 2.5 cm. Style length: About 2.5 cm. Style color: Close to 2D. Stigma diameter: About 4 mm. Stigma color: Close to 2D. Ovary color: Close to 10A.

*Fruits and seeds.*—Fruit and seed production have not been observed on plants of the new *Camellia* to date.

Garden performance: Plants of the new *Camellia* have been observed have good garden performance and to tolerate rain, wind, full sunlight and temperatures ranging from about −10° C. to about 40° C.

Pathogen & pest resistance: Plants of the new *Camellia* have not been observed to be resistant to pathogens and pests common to *Camellia* plants to date.

It is claimed:

1. A new and distinct cultivar of *Camellia* plant named 'HA5110' as illustrated and described.

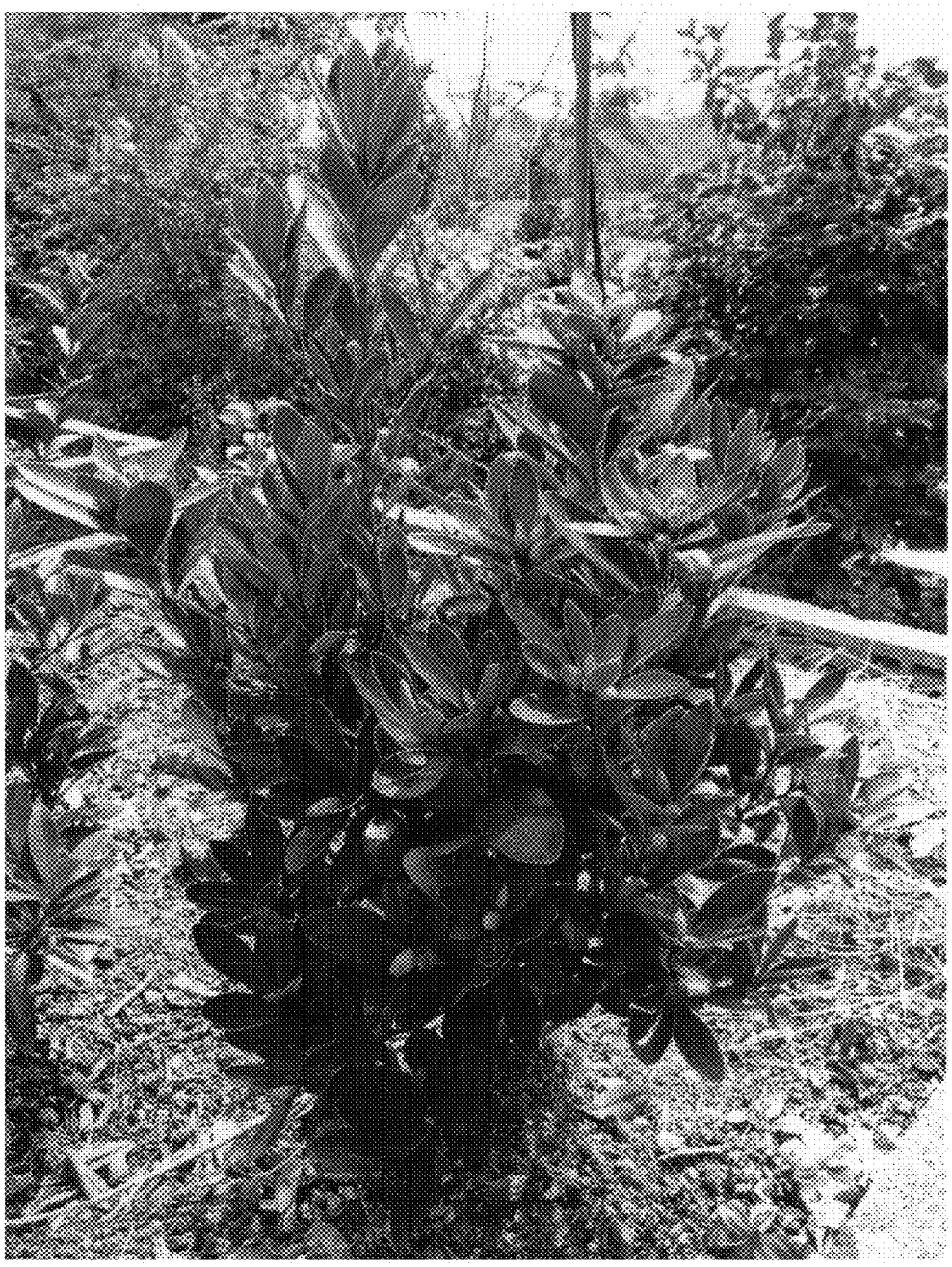

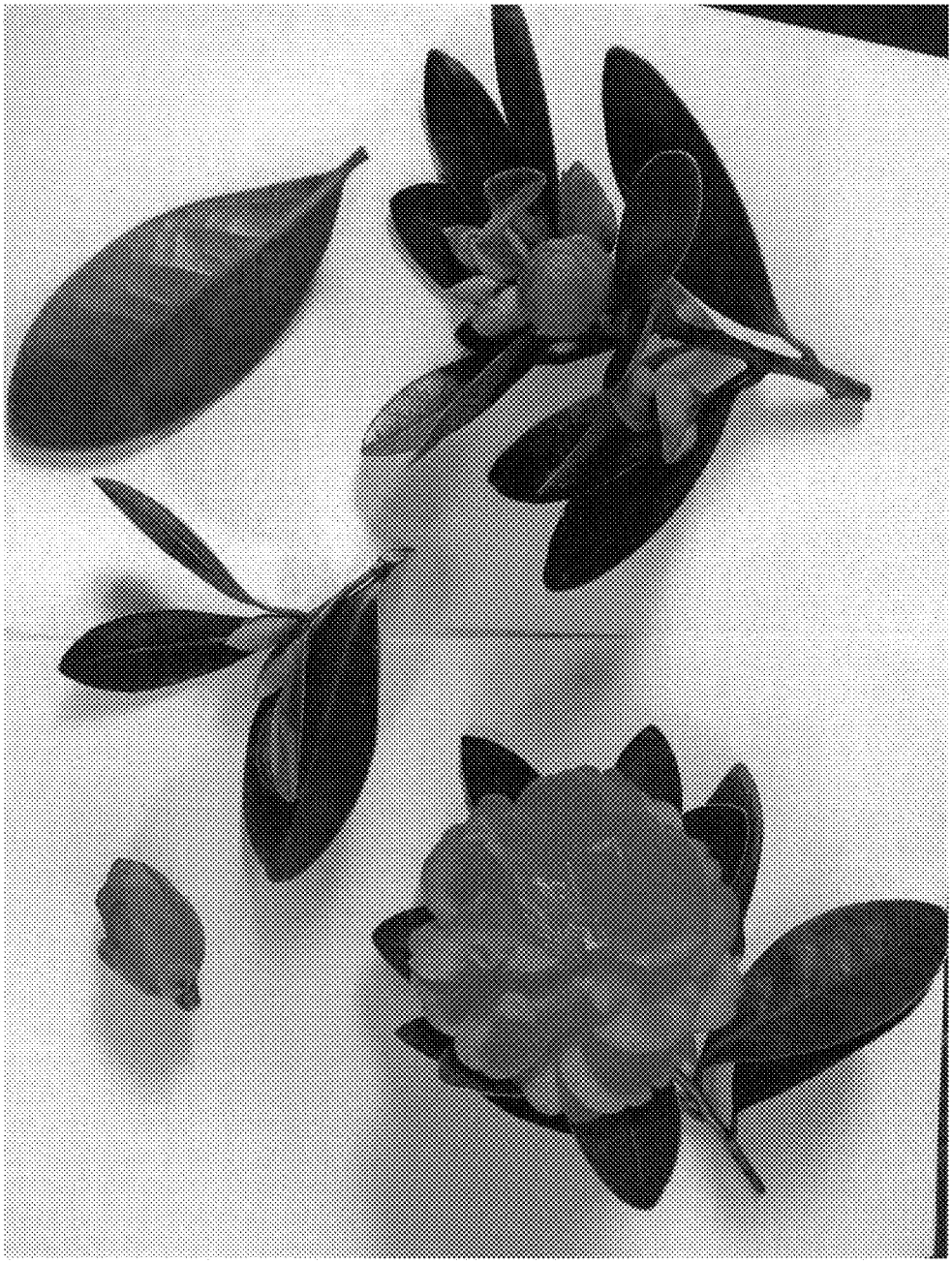

* * * * *